US00PP19027P2

(12) United States Plant Patent
Falcetti-Arnold

(10) Patent No.: US PP19,027 P2
(45) Date of Patent: Jul. 15, 2008

(54) ***EUPHORBIA* PLANT NAMED 'GLACIER BLUE'**

(50) Latin Name: *Euphorbia characias*
Varietal Denomination: Glacier Blue

(76) Inventor: Gina Falcetti-Arnold, 20724 Echo Hill Road, Sedro Woolley, WA (US) 98284

( * ) Notice: Subject to any disclaimer, the term of this patent is extended or adjusted under 35 U.S.C. 154(b) by 0 days.

(21) Appl. No.: 11/804,763

(22) Filed: May 21, 2007

(51) Int. Cl.
*A01H 5/00* (2006.01)

(52) U.S. Cl. ..... Plt./302

(58) Field of Classification Search ..... Plt./302
See application file for complete search history.

*Primary Examiner*—Kent L. Bell
*Assistant Examiner*—Annette H Para

(57) ABSTRACT

A new cultivar of *Euphorbia* plant named 'Glacier Blue' that is distinguishable by upright compact habit, variegated blue-grey and cream-white foliage, and blue-grey flower bracts with cream-white stripes. In combination these traits set 'Glacier Blue' apart from all other existing varieties of *Euphorbia* known to the inventor.

2 Drawing Sheets

Genus: *Euphorbia.*
Species: *characias.*
Denomination: 'Glacier Blue'.

BACKGROUND OF THE INVENTION

The present invention relates to a new and distinct cultivar of spurge, suitable for use in bed, border, and container as a specimen or accent plant. The new invention, in the Euphorbiaceae family, is known botanically as *Euphorbia characias,* and will be referred to hereinafter by the cultivar name 'Glacier Blue'.

The new *Euphorbia* cultivar named 'Glacier Blue' was discovered in Mount Vernon, Wash., as a naturally occurring branch sport of *Euphorbia* 'Tasmanian Tiger' (U.S. Plant Pat. No. 15,715). The inventor discovered and selected 'Glacier Blue' in 2004. The parent is an individual *Euphorbia* 'Tasmanian Tiger' that was growing in a commercial crop of clean stock 'Tasmanian Tiger' raised from tissue culture.

The closest comparison plant is 'Tasmanian Tiger'. The new *Euphorbia* variety named 'Glacier Blue' is distinguishable from 'Tasmanian Tiger' by robust growth, large sturdy stems, blue-grey leaf and flower bract color, and leaf margins that are narrow and whiter than all other variegated *Euphorbia* varieties known to the inventor. 'Glacier Blue' is less susceptible to burn than 'Tasmanian Tiger'.

'Glacier Blue' is robust and drought tolerant, exhibiting upright compact habit, variegated blue-grey foliage with narrow cream-white margins, and cream-white flower bracts, with blue-grey stripes. 'Glacier Blue' blooms late winter through spring. Cultural requirements are full sun, average well-draining soil, and moderate water. 'Glacier Blue' reaches 46 cm in height and 38 cm in width at maturity.

The first asexual reproduction of 'Glacier Blue' was conducted in 2004. Asexual propagation was accomplished by the inventor in Mount Vernon, Wash. using the method of stem cuttings. Since then the new *Euphorbia* cultivar named 'Glacier Blue' has been determined stable, fixed, and reproduces true to type in successive generations of asexual propagation.

SUMMARY OF THE INVENTION

The following traits have been repeatedly observed and represent the distinguishing characteristics of the new *Euphoriba* cultivar named 'Glacier Blue'. These traits in combination distinguish 'GLACIER BLUE' from all other existing varieties of *Euphorbia* known to the inventor. 'Glacier Blue' has not been tested under all possible conditions and phenotypic differences may be observed with variations in environmental, climatic, and cultural conditions, however, without any variance in genotype.

1. 'Glacier Blue' exhibits upright compact habit.
2. 'Glacier Blue' is robust and drought tolerant.
3. 'Glacier Blue' exhibits cream-white bracts with blue-grey stripes.
4. 'Glacier Blue' blooms late winter through spring.
5. 'Glacier Blue' exhibits variegated blue-grey foliage with cream-white margins.
6. 'Glacier Blue' exhibits sturdy stems.
7. 'Glacier Blue' is asexually propagated using the method of stem cuttings.
8. 'Glacier Blue' is hardy to USDA Zone 7.
9. 'Glacier Blue' reaches 46 cm in height and 38 cm in width.
10. 'Glacier Blue' is suitable as a specimen for bed, border or container.

BRIEF DESCRIPTION OF THE DRAWINGS

The accompanying color drawings illustrate the overall appearance of the new *Euphorbia* cultivar named 'Glacier Blue' showing color as true as it is reasonably possible to obtain in color reproductions of this type. Color in the drawings may differ from the color values cited in the detailed botanical description, which accurately describes the actual color of the new variety 'Glacier Blue'.

The drawing labeled

The drawing labeled

FIG. 1 and FIG. 2 were made using conventional techniques and although flower and foliage color may appear different from actual color due to light reflectance, they are as accurate as possible by conventional photography.

BOTANICAL DESCRIPTION OF THE PLANT

Figure 1:
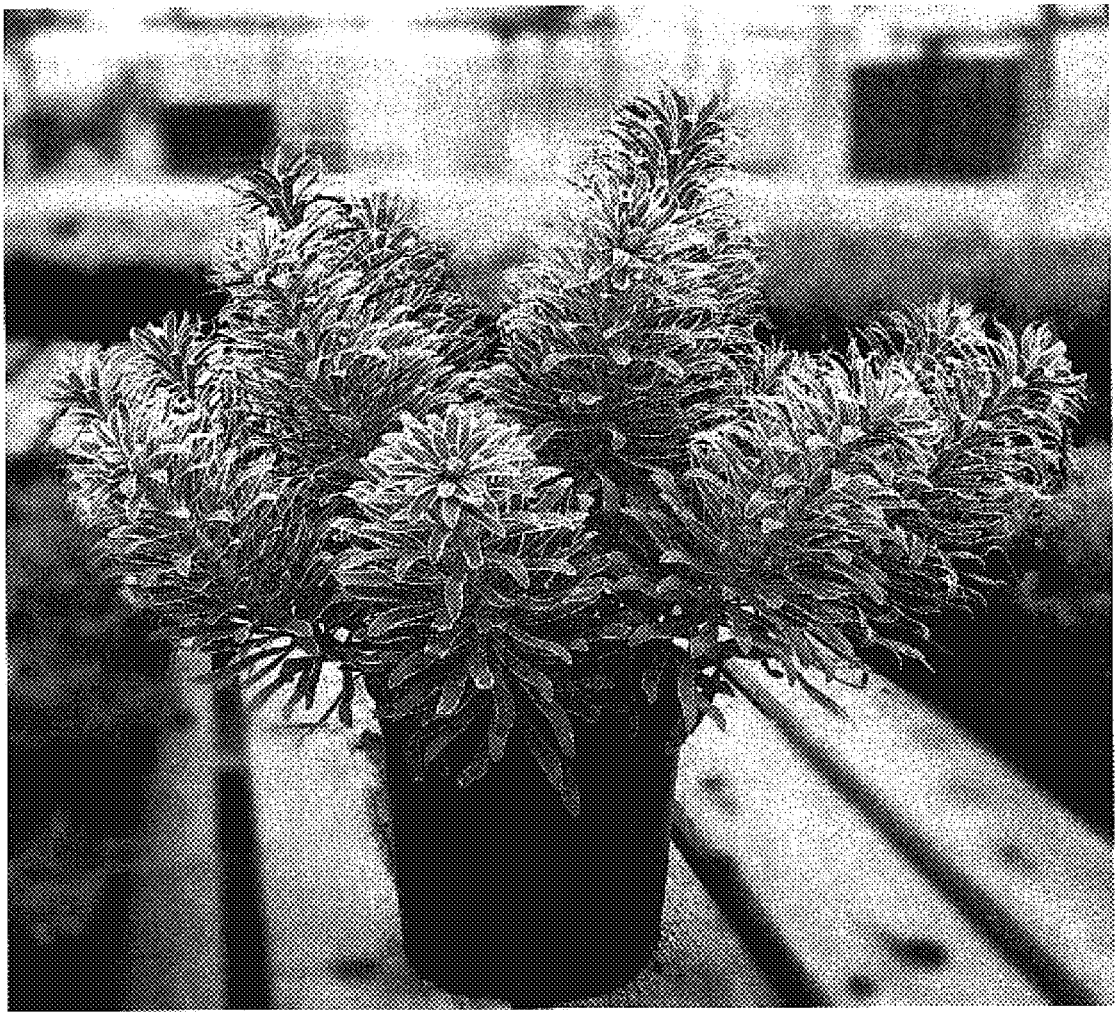
FIG. 1 depicts the whole plant in bloom from a side perspective.
Figure 2:
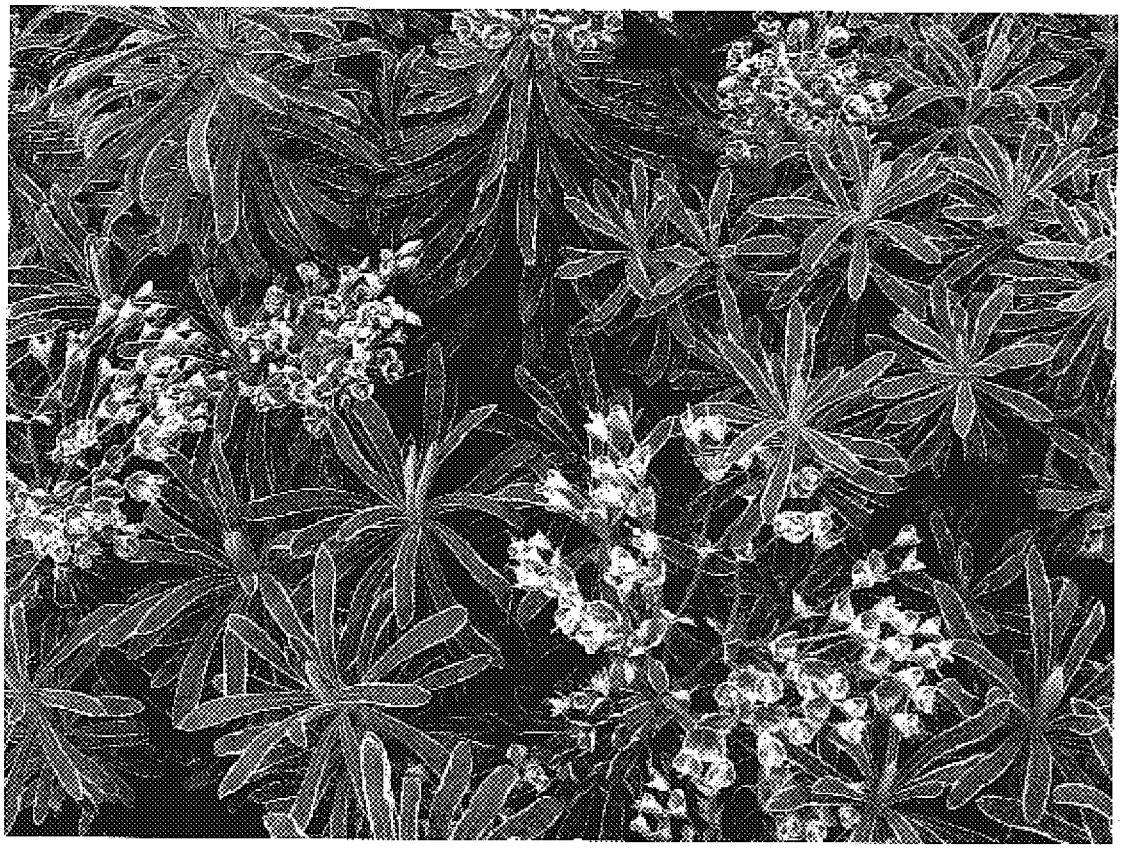
FIG. 2 depicts a view of the foliage and flower bracts.

The following is a detailed botanical description of the new *Euphorbia* cultivar named 'Glacier Blue'. Observations, measurements, values and comparisons were collected in Arroyo Grande, Calif. from 12-month-old, 2-liter container plants grown out-of-doors. Color determinations are made in accordance with the 2001 edition of The Royal Horticultural Society Colour Chart of London, England, except where general color terms of ordinary dictionary significance are used. The growing requirements of the new variety are similar to the species.

Botanical classification: *Euphorbia characias* 'Glacier Blue'.
Family: Euphorbiaceae.
Genus: *Euphorbia*.
Species: *characias*.
Denomination: 'Glacier Blue'.
Common name: Spurge.
Commercial classification: Sub-shrub.
Parentage: 'Glacier Blue' was discovered as a naturally occurring branch sport of *Euphorbia* 'Tasmanian Tiger' (U.S. Plant Pat. No. 15,715).
Asexual propagation method: Stem cuttings.
Rooting habit: Fine and fibrous.
Time to develop roots.—6–8 weeks are needed for roots to develop on an initial cutting.
Temperature recommended to develop roots: 18° Centigrade.
Crop time: 8–9 months are needed to produce a finished 1-liter container from a rooted cutting.
Habit: Upright compact habit.
Shape: Inverted pyramid.
Use: Bed, border, or container plant.
Type: Perennial.
Vigor: Vigorous.
Plant dimensions (at maturity): 46 cm in height and 38 cm in width.
Cultural requirements: Full sun, average well-draining soil, and moderate water.
Diseases and pests: Susceptible to spider mites, Thielaviopsis, and Pythium.
Hardiness: Hardy to USDA Zone 7.
Seasonal traits: Blooms February through May.
Special considerations: Hazardous. All parts exude a white milky substance when bruised that can be toxic and may elicit dermal irritation.
Stem:
- *Branching habit.*—Divergent.
- *Dimensions* (*average*).—11 cm in length and 0.75 cm in width.
- *Shape.*—Columnar.
- *Surface.*—Pubescent.
- *Color.*—146D.
- *Scar dimensions.*—1 mm in height and 0.25 cm in width.
- *Scar color.*—165B.
- *Scar shape.*—Spindle-shaped.
- *Internode length.*—0.75 cm.
- *Type.*—Evergreen.
- *Arrangement.*—Spiral.
- *Division.*—Simple.
- *Shape.*—Spatulate.
- *Length* (*average*).—6.50 cm.
- *Width* (*average*).—1 cm.
- *Leaf apex.*—Rounded.
- *Leaf base.*—Attenuate.
- *Quantity* (*range*).—50–70 leaves per stem.
- *Venation pattern* (*abaxial and adaxial surfaces*).—Pinnate with visible mid-vein.
- *Vein color* (*adaxial surface*).—191D.
- *Vein color* (*abaxial surface*).—191D.
- *Margin.*—Entire.
- *Surface* (*adaxial surface*).—Pubescent.
- *Surface* (*abaxial surface*).—Puberulent.
- *Attachment.*—Sessile.
- *Leaf color* (*adaxial surface*).—189A and 157D.
- *Leaf color* (*abaxial surface*).—191B and 157D.
- *Leaf fragrance.*—None observed.

Flower:
- *Blooming seasons.*—Late winter through spring.
- *Type of inflorescence.*—Cyathium.
- *Inflorescence shape.*—Cupule.
- *True perianth.*—Absent.
- *Staminate flower.*—Apetalous.
- *Pistillate flower.*—Apetalous.
- *Cyathia quantity* (*range per stem*).—80–160.
- *Cyathia quantity* (*average per rachis*).—6.
- *Cyathium dimensions.*—1.50 cm in width and 1.50 cm in length.
- *Aspect.*—Facing upward and outward.
- *Bud shape.*—Ovate.
- *Bud dimensions.*—0.50 cm in diameter and 0.70 cm in length.
- *Bud surface.*—Puberulent.
- *Bud color.*—189C and 157D.
- *Bud apex.*—Rounded.
- *Rachis color.*—146D.
- *Rachis dimensions* (*average*).—4.5 cm in length and 2 mm in diameter.
- *Rachis shape.*—Cylindrical.
- *Rachis surface.*—Puberulent.
- *Bract quantity* (*average*).—12 per rachis.
- *Bract fused or unfused.*—Unfused.
- *Bract color* (*adaxial surface*).—157D and N138C.
- *Bract color* (*abaxial surface*).—157D and N138D.
- *Bract margin.*—Entire.
- *Bract shape.*—Orbicular.
- *Bract apex.*—Obtuse.
- *Bract base.*—Rounded.
- *Bract dimensions.*—0.75 cm in length and 1 cm in width.
- *Bract surfaces* (*adaxial and abaxial*).—Puberulent.
- *Lastingness of cyathium* (*range*).—20–35 days.
- *Cyathium fragrance.*—Pungent color.

Reproductive organs:
- *Stamens.*—Fasciculate.
- *Stamen color.*—166D.
- *Stamen length.*—5 mm.
- *Anther length.*—<1 mm.
- *Anther color.*—166A.

*Pollen color.*—166B.
*Pollen quantity.*—Minimal.

*Pistil.*—1 in number.

*Pistil length.*—9 mm.
*Pistil color.*—166B.
*Style length.*—1 mm.
*Style color.*—166B.
*Stigma color.*—N199B.
*Stigma shape.*—Bi-fid.
*Stigma width.*—<0.50 mm.
*Ovary shape.*—Globular.
*Ovary dimensions.*—2.50 mm in height and 2.50 mmin diameter.
*Ovary surface.*—Woolly.
*Ovary color.*—166B.
*Ovary position.*—Superior.

Seed: No seed has been observed to date.

It is claimed:

1. A new and distinct cultivar of *Euphorbia* plant named 'Glacier Blue' as described and illustrated herein.

* * * * *